United States Patent [19]

Bostick et al.

[11] Patent Number: 5,215,547
[45] Date of Patent: Jun. 1, 1993

[54] MIDDLE DISTILLATE FUELS AND ADDITIVES THEREFOR

[75] Inventors: John G. Bostick, Smithton, Ill.; Lawrence J. Cunningham, Kirkwood, Mo.

[73] Assignee: Ethyl Petroleum Additives, Inc., Richmond, Va.

[21] Appl. No.: 756,578

[22] Filed: Sep. 9, 1991

[51] Int. Cl.$^5$ ............................................... C10L 1/22
[52] U.S. Cl. ...................................... 44/336; 544/180
[58] Field of Search .......................... 44/336; 544/180

[56] References Cited

U.S. PATENT DOCUMENTS

| | | | |
|---|---|---|---|
| 2,675,382 | 4/1954 | Melamed | 544/180 |
| 2,889,277 | 6/1959 | Hughes | 544/180 |
| 3,763,094 | 10/1973 | Knell et al. | 44/336 |
| 3,884,917 | 5/1975 | Ibbotson | 544/180 |
| 3,915,970 | 10/1975 | Limaye et al. | 44/336 |
| 4,585,462 | 4/1986 | Kitchen, III | 44/336 |

Primary Examiner—Jacqueline Howard
Attorney, Agent, or Firm—David E. LaRose

[57] ABSTRACT

This invention relates to novel hexahydrotriazine compounds, a process for their production and their use as additives for fuels and oleaginous fluids.

17 Claims, No Drawings

MIDDLE DISTILLATE FUELS AND ADDITIVES THEREFOR

TECHNICAL FIELD

This invention relates to novel hexahydrotriazine compounds, to a process for their production, and to their use as additives for fuels and oleaginous fluids, especially middle distillate fuels.

The Invention

Provided by this invention is one or a mixture of substituted hexahydrotriazines of the formula

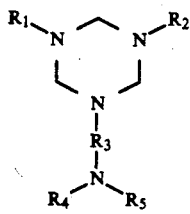

wherein $R_1$ is a hydrocarbyl group, preferably a cycloalkyl group, most preferably a cyclohexyl group; $R_2$ is either a hydrocarbyl group, preferably a cycloalkyl group, most preferably a cyclohexyl group or a dihydrocarbylaminoalkyl group, preferably a dialkylaminoalkyl group, most preferably a dimethylaminopropyl group; $R_3$ is an alkylene group having up to 12 carbon atoms, preferably an alkylene group having 2 to 10 carbon atoms, most preferably a trimethylene (propylene) group; and $R_4$ and $R_5$ are hydrocarbyl groups having from 1 to 20 carbon atoms, preferably alkyl groups, most preferably methyl groups.

The compounds of this invention are effective stabilizers for oleaginous liquids such as natural and synthetic oils of lubricating viscosity, and liquid petroleum-based fuels such as gasoline, and fuels heavier than gasoline such as middle distillate fuels and fuel oils (e.g., diesel fuels, burner fuels, jet fuels, heating gas oils, cycle gas oils, vacuum gas oils, etc.), and residual fuels. This invention thus provides in one of its embodiments, a liquid hydrocarbonaceous fluid containing a minor stabilizing amount of one or a mixture of compounds of this invention. Such compositions may also include other known conventional additives of the types useful in the type of hydrocarbonaceous liquid being used.

This invention also provides a concentrate for use in oleaginous liquids which comprise from about 0.1 to 99.9 percent by weight of one or more of the substituted hexahydrotriazines of this invention and from about 99.9 to about 0.1 percent by weight of a solvent or diluent for the hexahydrotriazine(s) which is miscible and/or capable of dissolving in the oleaginous liquid in which the concentrate is to be used.

Preferred compositions of this invention comprise liquid hydrocarbonaceous fuels heavier than gasoline containing a minor stabilizing amount of at least one hexahydrotriazine as disclosed herein. Such fuels include residual fuels, kerosene, jet fuels, heating oils, diesel fuels, light gas oil, heavy gas oil, light cycle gas oils, heavy cycle gas oils, vacuum gas oils, and the like. Most preferably the fuel is a middle distillate fuel such as a diesel fuel, kerosene, jet fuels, house heating oil or the like. Such middle distillates usually boil in the range of 350° to 700° F. and have cloud points typically in the range of −78° F. to about 45° F. The hydrocarbon stock can comprise straight run and thermally and/or catalytically cracked distillates. Oxygenated blending components of suitable distillation characteristics such as heavy ethers, alcohols and/or esters boiling within the boiling range of the middle distillate itself can be present in minor amounts in the fuel composition(s).

Particularly desirable additive combinations for use in such hydrocarbonaceous middle distillate fuels include the following:

(a) a combination comprising at least one hexahydrotriazine of this invention and at least one metal deactivator, preferably an N,N'-disalicylidene-1,2-alkane diamine such as N,N'-disalicylidene-1,2-ethane diamine, N,N'-disalicylidene-1,2-butane diamine, N,N'-disalicylidene-1,2-cyclohexane diamine, etc., and most preferably N,N'-disalicylidene-1,2-propane diamine;

(b) the combination of a) above further including at least one N,N-dialkyl-N-cycloalkylamine, such as N,N-diethyl-N-cyclohexylamine, N,N-dibutyl-N-cyclohexylamine, N,N-dihexyl-N-cyclohexylamine, N,N-di(2-ethylhexyl)N-cyclohexylamine, N,N-didecyl(N-cyclohexylamine), N,N-didodecyl-N-cyclohexylamine, N,N-dimethyl-N-methylcyclohexylamine, N,N-dimethyl-N-dimethylcyclohexylamine, N,N-diethyl-N-cyclopentylamine, N,N-diisopropyl-N-cycloheptylamine, N,N-dipentyl-N-cyclooctylamine and most preferably N,N-dimethyl-N-cyclohexylamine;

(c) the combination of a) above further including (i) at least one N-(2,6-dialkyl-4-hydroxybenzyl) hexahydropyrimidine or (ii) at least one N,N-bis(2,6-dialkyl-4-hydroxybenzyl)hexahydropyrimidine, or (iii) a mixture of (i) and (ii), wherein the alkyl groups contain up to about 18 carbon atoms and preferably include at least one tertiary alkyl group, and most preferably are all tertiary alkyl groups, especially tertiary butyl groups. The synthesis of such compounds involves reacting a 2,6-dialkylphenol, formaldehyde (or a formaldehyde source such as formalin, etc.) and 1,3-propanediamine in molar ratios of about 1 to 2 moles of dialkylphenol and about 2 to 3 moles of formaldehyde per mole of 1,3-proponediamine at a temperature in the range of 60° to 100° C., such as in refluxing isopropanol.

The compounds of this invention can be prepared by reacting in appropriate proportions at least one primary monoamine (preferably a cycloalkylamine, most preferably cyclohexylamine), formaldehyde or a formaldehyde source (e.g., paraformaldehyde), and an N,N-dihydrocarbyl alkylene diamine (preferably an N,N-dialkyl alkylene diamine, most preferably N,N-dimethyl-1,3-propane diamine).

By varying the proportions of the reactants, the composition of the product can be varied. For example, reaction among 2 moles of monoamine and 3 moles of formaldehyde per mole of the diamine yields a product enriched in product of the above formula in which $R_1$ and $R_2$ are both hydrocarbyl groups corresponding to the hydrocarbyl group of the monoamine. On the other hand, when 2 moles of the diamine and 3 moles of formaldehyde are reacted per mole of the monoamine, the product is enriched in hexahydrotriazine of the above formula where $R_1$ is a hydrocarbyl group corresponding to the hydrocarbyl group of the monoamine, and $R_2$ corresponds to $-R_3-N(R_4)(R_5)$. Proportions intermediate to those presented above give rise to mixtures of varying proportions of both such products. Thus in the process of this invention the reactants are generally employed in mole ratios of from about 0.5 to about 2.5 moles of the monoamine(s) and from about 2.5 to about 0.5 moles of the diamine(s) per each 3 moles of HCHO entering into the reaction. Normally an excess of formaldehyde or formaldehyde-producing reactant is employed.

Reaction temperatures in the range of from about 0° to 30° C. are usually employed, although departures may be made from these ranges whenever deemed necessary or advisable. All that is required is to maintain the reactants at a temperature at which reaction proceeds at a suitable rate and without causing decomposition of the desired product or product mixture.

The reaction may be conducted in bulk or in a suitable inert liquid reaction medium such as a paraffinic or cycloparaffinic or aromatic hydrocarbon solvent, an ether solvent, a halogenated hydrocarbon solvent, or the like.

Usually the formaldehyde reactant is charged to the reaction vessel either concurrently with or subsequent to the charging of the amine reactants. Water formed in the reaction is removed from the reaction mixture either essentially as soon as the water is formed, or after completion of the reaction.

Illustrative primary monoamines for use in the process include $C_1$ to $C_{100}$, preferably $C_2$ to $C_{24}$, most preferably $C_4$ to $C_{18}$ alkyl or alkenyl amines in which the alkyl or alkenyl group may be straight chain or branched, but rot of tertiary configuration; $C_4$ to $C_{40}$, preferably $C_5$ to $C_{18}$, most preferably $C_6$ to $C_{10}$ cycloalkyl or cycloalkenyl amines; $C_6$ to $C_{40}$, preferably $C_6$ to $C_{18}$, most preferably $C_6$ to $C_{14}$ aryl amines; or mixtures thereof. The principal requirement for this reactant is that amino group should not be sufficiently sterically hindered as to prevent the cyclization-condensation reaction from occurring.

Typical diamines for use in the process are those having the formula $H_2N-R_3-N(R_4)(R_5)$ wherein $R_3$, $R_4$ and $R_5$ are as described above. $R_3$ may be an unsubstituted straight chain alkylene group or it may contain one or more side chains. $R_4$ and $R_5$ can be alkyl, alkenyl, cycloalkyl, aralkyl, aryl, alkaryl, or like hydrocarbyl groups containing up to about 100 carbon atoms, preferably up to about 24 carbon atoms, more preferably 1 to 10 carbons atoms, and most preferably are methyl groups. Individual diamines of this type are usually used, but mixtures of two or more such diamines can be used, if desired.

The following examples, in which parts and percentages are by weight, illustrate the process of this invention and the products formed thereby.

EXAMPLE 1

Formaldehyde (37%, 89.2 parts) is charged to a reaction vessel equipped with cooling and heating means and a condenser. A preformed mixture of 66.I parts of cyclohexylamine and 34.0 parts of N,N-dimethyl-1,3-propane diamine is then added to the reaction vessel over a period of 30 minutes while maintaining the temperature below 30° C. After this, the mixture is heated to distill off the water and excess formaldehyde. The product contains as the principal component 1,3-dicyclohexyl-5-(N,N-dimethyl-3'-amino-propyl) hexahydrotriazine.

EXAMPLE 2

The procedure of Example 1 is repeated except that 33.0 parts of cyclohexylamine and 68 parts of N,N-dimethyl-1,3-propane diamine are employed. The principal product is 1-cyclohexyl-3,5-di-(N,N-dimethyl-3'-aminopropyl)hexahydrotriazine.

EXAMPLE 3

To a reactor equipped as in Example 1 are added 264.2 parts of cyclohexylamine, 136 parts of N,N-dimethyl-1,3-propane diamine and 175 parts of toluene. To this mixture is added 327 parts of 37% aqueous formaldehyde solution over a period of 20 minutes while keeping the temperature between 20° and 34° C. Then the mixture is heated to remove the water in the form of a toluene-water azeotrope. During this separation procedure additional toluene is periodically added as required. Initially the temperatures are kept at about 58°-65° C. Thereafter a vacuum is gradually applied while slowly increasing the temperature until the temperature reaches 94° C. at 63mm Hg pressure. At this point the separation is discontinued. The residual product is predominantly 1,3-dicyclohexyl-5-(N,N-dimethyl-3-aminopropyl)hexahydrotriazine.

EXAMPLE 4

The procedure of Example 3 is repeated using an equivalent quantity of lauryl amine in place of cyclohexylamine. The principal product is 1,3-dilauryl-5-(N,N-dimethyl-3'-diaminopropyl)hexahydrotriazine.

EXAMPLE 5

A product composed predominantly of 1,3-dioleyl-5-(N,N-diethyl-3'-aminopropyl)hexahydrotriazine is formed by reacting 2 moles of oleylamine and 1 mole of N,N-diethyl-1,3-propane diamine with 3 moles of formaldehyde while controlling the temperatures to between 20° and 30° C.

EXAMPLE 6

The procedure of Example 5 is repeated using 1.5 moles of each of the amine reactants. The product includes both 1,3-dioleyl-5-(N,N-diethyl-3'-aminopropyl)hexahydrotriazine and 1-oleyl-3,5-di-(N,N-diethyl-3'-aminopropyl)hexahydrotriazine.

EXAMPLE 7

Reaction at 20° to 30° C. among 2 moles of aniline, 1 mole of N,N-dibutyl-1,3-propane diamine and 3 moles of formaldehyde yields a product composed mainly of 1,3-diphenyl-5-(N,N-dibutyl-3'-aminopropyl) hexahydrotriazine.

EXAMPLE 8

Repetition of Example 7 using 2 moles of benzyl amine in place of the aniline forms a product composed mainly of 1,3-dibenzyl-5-(N,N-dibutyl-3'-aminopropyl)-hexahydrotriazine.

EXAMPLE 9

Example 7 is repeated using 2 moles of 2-phenylethyl amine in lieu of 2 moles of aniline whereby a product composed chiefly of 1,3-di-(phenethyl)-5-(N,N-dibutyl-3'-aminopropyl)hexahydrotriazine is formed.

EXAMPLE 10

Example 3 is repeated except that an equivalent amount of decyloxypropyl amine replaces the cyclohexylamine. The product contains 1,3-di-(decyloxypropyl)-5-(N,N-dimethyl-3'-aminopropyl)hexahydrotriazine.

Other compounds of this invention include, for example, the following:
- 1,3-diethyl-5-(N,N-dimethyl-3'-aminopropyl)hexahydrotriazine,
- 1,3-diisopropyl-5-(N,N-dimethyl-3'-aminopropyl)-hexahydrotriazine,
- 1,3-dibutyl-5-(N,N-dimethyl-3'-aminopropyl)hexahydrotriazine,
- 1,3-di-2-ethylhexyl-5-(N,N-dimethyl-3'-aminopropyl)hexahydrotriazine, 1,3-di-tetradecyl-5-(N,N-dimethyl-3'-aminopropyl)hexahydrotriazine, 1-decyl-3-octyl-5-(N,N-dimethyl-3'-aminopropyl)-hexahydrotriazine, 1,3-diallyl-5-(N,N-dimethyl-3'-amino-propyl)hexahydrotriazine, 1,3-di-(4-methylcyclohexyl)-5-(N,N-dimethyl-3'-aminopropyl)hexahydrotriazine, 1-cyclohexyl-3-phenyl-5-(N,N-dimethyl-3'-aminopropyl)hexahydrotriazine, 1,3-di(polypropenyl)-5-(N,N-dimethyl-3'-aminopropyl)hexahydrotriazine,
- 1,3-dibenzyl-5-(N,N-dimethyl-3'-aminopropyl)hexahydrotriazine
- 1,3-diphenyl-5-(N,N-dimethyl-3'-aminopropyl)hexahydrotriazine, 1,3-di-m-tolyl-5-(((N,N-dimethyl-3'-aminopropyl)hexahydrotriazine, 1,3-dipropyl-5-(N,N-dibutyl-3'-aminopropyl)hexahydrotriazine, 1,3-diphenyl-5-(N,N-dioctyl-4'-aminobutyl)hexahydrotriazine, 1,3-di(polybutenyl)-5-(N,N-dimethyl-3'-aminopropyl)hexahydrotriazine, and the like.

ASTM D-4625 Storage Stability Test

The color of freshly filtered middle distillate fuel (400 mL) is determined utilizing the ASTM D-1500 method and then the fuel is stored in a suitable container in a darkened area at 43° C. for 13 weeks. After the storage period the color of the fuel is again determined using ASTM D-1500. The deposits are obtained by filtering the fuel and by combining any deposits on the filter media with any deposit that adhered to the walls of the fuel container. The deposits are reported as mg/100 mL of sample.

Accelerated Storage Stability Test (F21-61)

Freshly filtered middle distillate fuel (50 mL) is heated at 149° C. for about 90 minutes. The sample is allowed to cool to room temperature in the dark and the color is determined using the ASTM D-1500 method. The sample is then filtered using a 4.25 cm Whatman #1 filter paper and the filtrate discarded. The filter paper is washed clean of fuel and the deposits are determined by comparing the filter paper containing the deposits to a set of reference filter papers.

To determine the effectiveness of the hexahydrotriazine compounds of this invention as a fuel stabilizer, additive compositions comprising, N,N-dimethylcyclohexylamine (DMCA), N,N-disalicylidene-1,2-propylenediamine (MDA), and 1,3-dicyclohexyl-5-(N,N-dimethyl-3'-aminopropyl)hexahydrotriazine (HHT) in the amounts indicated in columns 2, 3, and 4 of the ensuing tables are added to fuels from various sources. These fuel mixtures are then subjected to the ASTM D-4625 storage stability test and the accelerated storage stability test as described above. Fuels which are already quite stable as determined by the foregoing stability tests, benefit less from the addition of additives than fuels which are less stable.

EXAMPLE 11

Fuel compositions of Table 1 utilize a base fuel which was obtained from Pennsylvania Crude. The stability of the base (unadditized) fuel is illustrated by Sample 1. Samples 6–8 of Table 1, illustrate the long and short term stability of fuel compositions containing all three additive components (i.e. DMCA, MDA, HHT) in combination with the fuel of Sample 1.

TABLE 1

| | Fuel Additive Composition (lbs/1000 Barrels) | | | Storage Stability Data | | | |
|---|---|---|---|---|---|---|---|
| | | | | F-21-61 (149° C.) | | ASTM D-4625 (43° C.) | |
| Sample | DMCA[1] | MDA[2] | HHT[3] | Color | Deposits | Color | Deposits (mg/1000 mL) |
| 1 | 0.00 | 0.00 | 0.00 | >8.0 | 17.0 | <3.5 | 6.7 |
| 2 | 0.00 | 0.13 | 0.00 | >8.0 | 18.0 | <3.5 | 6.7 |
| 3 | 0.00 | 0.25 | 0.00 | >8.0 | 17.0 | <3.5 | 7.9 |
| 4 | 0.00 | 0.50 | 0.00 | <8.0 | 13.0 | 3.0 | 5.4 |
| 5 | 0.00 | 1.25 | 0.00 | 7.5 | 13.0 | <3.5 | 4.7 |
| 6 | 1.75 | 0.13 | 0.62 | <4.0 | 10.0 | 3.0 | 3.3 |
| 7 | 3.50 | 0.25 | 1.25 | 2.5 | 7.0 | <3.0 | 2.8 |
| 8 | 7.00 | 0.50 | 2.50 | 2.0 | 4.0 | <3.0 | 2.4 |
| 9 | 17.50 | 1.25 | 6.25 | 1.5 | 4.0 | <3.0 | 2.5 |
| 10 | 2.38 | 0.12 | 0.00 | 4.5 | 13.0 | <3.5 | 4.8 |
| 11 | 4.75 | 0.25 | 0.00 | 3.0 | 10.0 | <3.5 | 4.0 |
| 12 | 9.50 | 0.50 | 0.00 | <2.5 | 6.0 | <3.5 | 3.0 |
| 13 | 23.75 | 1.25 | 0.00 | 1.5 | 2.0 | <3.5 | 2.2 |
| 14 | 0.00 | 0.13 | 2.37 | 8.0 | 16.0 | <3.5 | 6.3 |
| 15 | 0.00 | 0.25 | 4.75 | <4.0 | 8.0 | 3.0 | 4.1 |
| 16 | 0.00 | 0.50 | 9.50 | <2.5 | 7.0 | <3.0 | 3.6 |
| 17 | 0.00 | 1.25 | 23.75 | 2.0 | 6.0 | 3.0 | 4.0 |

[1]DMCA = N,N-dimethylcyclohexylamine
[2]MDA = N,N-disalicylidene-1,2-propylenediamine
[3]HHT = 1,3-dicyclohexyl-5-(N,N-dimethyl-3'-aminopropyl)hexahydrotriazine

EXAMPLE 12

Fuel compositions of Table 2 utilize a base fuel which was obtained from a Midcontinent Crude (typical No. 2 Diesel Fuel). The stability of the base (unadditized) fuel is illustrated by Sample 1. Samples 5–6 of Table 2, illustrate the long and short term stability of fuel compositions containing all three additive components (i.e. DMCA, MDA, HHT) in combination with the fuel of Sample 1.

TABLE 3

| | Fuel Additive Composition (lbs/1000 Barrels) | | | Storage Stability Data | | | |
|---|---|---|---|---|---|---|---|
| | | | | F-21-61 (149° C.) | | ASTM D-4625 (43° C.) | |
| Sample | DMCA[1] | MDA[2] | HHT[3] | Color | Deposits | Color | Deposits (mg/1000 mL) |
| 1 | 0.00 | 0.00 | 0.00 | 3.0 | 2.0 | 7.0 | 5.8 |
| 2 | 0.00 | 0.50 | 0.00 | <3.0 | 2.0 | <7.0 | 5.2 |
| 3 | 7.00 | 0.50 | 2.50 | <2.5 | 2.0 | 5.5 | 1.1 |
| 4 | 14.0 | 1.00 | 5.00 | <2.5 | 2.0 | <6.0 | 1.0 |
| 5 | 9.50 | 0.50 | 0.00 | <2.5 | 2.0 | <6.0 | 0.8 |
| 6 | 19.0 | 1.00 | 0.00 | <2.5 | 2.0 | 6.0 | 1.3 |
| 7 | 0.00 | 0.50 | 9.50 | <3.0 | 4.0 | 5.5 | 3.4 |
| 8 | 0.00 | 1.00 | 19.00 | <3.0 | 3.0 | 5.0 | 3.1 |

[1] DMCA = N,N-dimethylcyclohexylamine
[2] MDA = N,N-disalicylidene-1,2-propylenediamine
[3] HHT = 1,3-dicyclohexyl-5-(N,N-dimethyl-3'-aminopropyl)hexahydrotriazine DMCA, MDA, HHT) in combination with the fuel of Sample 1.

TABLE 2

| | Fuel Additive Composition (lbs/1000 Barrels) | | | Storage Stability Data | | | |
|---|---|---|---|---|---|---|---|
| | | | | F-21-61 (149° C.) | | ASTM D-4625 (43° C.) | |
| Sample | DMCA[1] | MDA[2] | HHT[3] | Color | Deposits | Color | Deposits (mg/1000 mL) |
| 1 | 0.00 | 0.00 | 0.00 | 5.0 | 8.0 | <5.0 | 3.5 |
| 2 | 0.00 | 0.15 | 0.00 | <5.0 | 8.0 | <5.0 | 3.1 |
| 3 | 2.85 | 0.15 | 0.00 | 4.5 | 7.0 | 4.5 | 2.8 |
| 4 | 5.7 | 0.3 | 0.00 | 3.0 | 5.0 | 4.0 | 1.6 |
| 5 | 2.10 | 0.15 | 0.75 | <3.5 | 5.0 | 4.0 | 1.6 |
| 6 | 4.20 | 0.30 | 1.50 | 2.5 | 3.0 | <4.0 | 0.8 |
| 7 | 0.00 | 0.15 | 2.85 | <3.5 | 7.0 | 4.0 | 1.9 |
| 8 | 0.00 | 0.30 | 5.70 | 3.0 | 4.0 | <4.0 | 1.4 |

[1] DMCA = N,N-dimethylcyclohexylamine
[2] MDA = N,N-disalicylidene-1,2-propylenediamine
[3] HHT = 1,3-dicyclohexyl-5-(N,N-dimethyl-3'-aminopropyl)hexahydrotriazine

EXAMPLE 13

Fuel compositions of Table 3 utilize a base fuel which was obtained from a Midcontinent Crude (Light Cycle Oil only). The stability of the base (unadditized) fuel is illustrated by Sample 1. Samples 3-4 of Table 3, illustrate the long and short term stability of fuel compositions containing all three additive components (i.e. DMCA, MDA, HHT) in combination with the fuel of Sample 1.

EXAMPLE 14

Fuel compositions of Table 4 utilize a base fuel which was obtained from Illinois Basin Crude. The stability of the base (unadditized) fuel is illustrated by Sample 1. Samples 6-9 of Table 4, illustrate the long and short term stability of fuel compositions containing all three additive components (i.e. DMCA, MDA, HHT) in combination with the fuel of Sample 1.

TABLE 4

| | Fuel Additive Composition (lbs/1000 Barrels) | | | Storage Stability Data | | | |
|---|---|---|---|---|---|---|---|
| | | | | F-21-61 (149° C.) | | ASTM D-4625 (43° C.) | |
| Sample | DMCA[1] | MDA[2] | HHT[3] | Color | Deposits | Color | Deposits (mg/1000 mL) |
| 1 | 0.00 | 0.00 | 0.00 | 6.0 | 7.0 | <5.0 | 9.2 |
| 2 | 0.00 | 0.13 | 0.00 | <6.0 | 7.0 | <5.0 | 11.3 |
| 3 | 0.00 | 0.25 | 0.00 | <6.0 | 7.0 | <5.0 | 9.2 |
| 4 | 0.00 | 0.50 | 0.00 | 6.5 | 8.0 | <5.0 | 7.1 |
| 5 | 0.00 | 1.25 | 0.00 | 8.0 | 13.0 | <5.0 | 9.2 |
| 6 | 1.75 | 0.13 | 0.62 | 4.5 | 10.0 | <4.0 | 5.2 |
| 7 | 3.50 | 0.25 | 1.25 | <3.5 | 7.0 | <4.0 | 3.9 |
| 8 | 7.00 | 0.50 | 2.50 | <3.0 | 5.0 | <4.0 | 3.1 |
| 9 | 17.50 | 1.25 | 6.25 | <3.0 | 5.0 | <4.0 | 3.7 |
| 10 | 2.38 | 0.12 | 0.00 | <6.5 | 7.0 | <4.0 | 4.0 |
| 11 | 4.75 | 0.25 | 0.00 | <3.5 | 5.0 | <4.0 | 3.0 |
| 12 | 9.50 | 0.50 | 0.00 | <2.5 | >1.0 | 4.0 | 3.2 |
| 13 | 23.75 | 1.25 | 0.00 | <2.5 | >1.0 | 4.0 | 2.6 |
| 14 | 0.00 | 0.13 | 2.37 | 6.0 | 11.0 | 5.0 | 10.7 |
| 15 | 0.00 | 0.25 | 4.75 | <4.0 | 8.0 | 4.5 | 5.8 |
| 16 | 0.00 | 0.50 | 9.50 | <3.0 | 6.0 | <4.0 | 3.7 |

TABLE 4-continued

| | Fuel Additive Composition (lbs/1000 Barrels) | | | Storage Stability Data | | | |
|---|---|---|---|---|---|---|---|
| | | | | F-21-61 (149° C.) | | ASTM D-4625 (43° C.) | |
| Sample | DMCA[1] | MDA[2] | HHT[3] | Color | Deposits | Color | Deposits (mg/1000 mL) |
| 17 | 0.00 | 1.25 | 23.75 | <3.0 | 6.0 | <3.5 | 3.5 |

[1]DMCA = N,N-dimethylcyclohexylamine
[2]MDA = N,N-disalicylidene-1,2-propylenediamine
[3]HHT = 1,3-dicyclohexyl-5-(N,N-dimethyl-3'-aminopropyl)hexahydrotriazine

EXAMPLE 15

Fuel compositions of Table 5 utilize a base fuel which was obtained from Southwest Kansas and/or West Texas Sour Crude. The stability of the base (unadditized) fuel is illustrated by Sample 1. Samples 3–4 of Table 5, illustrate the long and short term stability of fuel compositions containing all three additive components (i.e. DMCA, MDA, HHT) in combination with the fuel of Sample 1.

EXAMPLE 16

Fuel compositions of Table 6 utilize a base fuel which was obtained from Illinois Basin Crude. The stability of the base (unadditized) fuel is illustrated by Sample 1. Samples 4–7 of Table 6, illustrate the long and short term stability of fuel compositions containing HHT or HHT and MDA in combination with the fuel of Sample 1.

TABLE 6

| | Fuel Additive Composition (lbs/1000 Barrels) | | | Storage Stability Data | | | |
|---|---|---|---|---|---|---|---|
| | | | | F-21-61 (149° C.) | | ASTM D-4625 (43° C.) | |
| Sample | DMCA[1] | MDA[2] | HHT[3] | Color | Deposits | Color | Deposits (mg/1000 mL) |
| 1 | 0.00 | 0.00 | 0.00 | 4.5 | 8.0 | 3.5 | 4.1 |
| 2 | 5.25 | 0.38 | 1.87 | <4.5 | 5.0 | 3.5 | 3.7 |
| 3 | 10.50 | 0.75 | 3.75 | <3.5 | 2.0 | 3.0 | 2.0 |
| 4 | 0.00 | 0.00 | 7.50 | <2.5 | 2.0 | <3.0 | 1.4 |
| 5 | 0.00 | 0.00 | 15.00 | <2.5 | >1.0 | 2.5 | 1.5 |
| 6 | 0.00 | 0.37 | 7.13 | <3.0 | 2.0 | <3.0 | 1.6 |
| 7 | 0.00 | 0.75 | 14.25 | <2.5 | 2.0 | <3.0 | 1.5 |
| 8 | 7.13 | 0.37 | 0.00 | <4.0 | 5.0 | 3.5 | 2.4 |
| 9 | 14.25 | 0.75 | 0.00 | <4.0 | 6.0 | <4.0 | 2.7 |

[1]DMCA = N,N-dimethylcyclohexylamine
[2]MDA = N,N-disalicylidene-1,2-propylenediamine
[3]HHT = 1,3-dicyclohexyl-5-(N,N-dimethyl-3'-aminopropyl)hexahydrotriazine

TABLE 5

| | Fuel Additive Composition (lbs/1000 Barrels) | | | Storage Stability Data | | | |
|---|---|---|---|---|---|---|---|
| | | | | F-21-61 (149° C.) | | ASTM D-4625 (43° C.) | |
| Sample | DMCA[1] | MDA[2] | HHT[3] | Color | Deposits | Color | Deposits (mg/1000 mL) |
| 1 | 0.00 | 0.00 | 0.00 | <2.5 | 6.0 | 2.5 | 2.2 |
| 2 | 0.00 | 0.13 | 0.00 | <2.5 | 5.0 | <2.5 | 1.4 |
| 3 | 1.75 | 0.13 | 0.62 | <2.5 | 5.0 | <2.5 | 1.4 |
| 4 | 3.50 | 0.25 | 1.25 | <2.5 | 4.0 | <2.5 | 1.1 |
| 5 | 0.00 | 0.13 | 2.37 | 2.0 | 4.0 | <2.5 | 1.4 |
| 6 | 0.00 | 0.25 | 4.75 | <2.5 | 4.0 | <2.5 | 1.5 |
| 7 | 2.37 | 0.13 | 0.00 | 2.0 | 4.0 | <2.5 | 2.0 |
| 8 | 4.75 | 0.25 | 0.00 | 2.5 | 4.0 | <2.5 | 1.3 |

[1]DMCA = N,N-dimethylcyclohexylamine
[2]MDA = N,N-disalicylidene-1,2-propylenediamine
[3]HHT = 1,3-dicyclohexyl-5-(N,N-dimethyl-3'-aminopropyl)hexahydrotriazine

EXAMPLE 17

Fuel compositions of Table 7 utilize a base fuel which was obtained from a mid-west refinery. The stability of the base (unadditized) fuel is illustrated by Sample 1.

TABLE 7

| | Fuel Additive Composition (lbs/1000 Barrels) | | | Storage Stability Data | | | |
|---|---|---|---|---|---|---|---|
| | | | | F-21-61 (149° C.) | | ASTM D-4625 (43° C.) | |
| Sample | DMCA[1] | MDA[2] | HHT[3] | Color | Deposits | Color | Deposits (mg/1000 mL) |
| 1 | 0.00 | 0.00 | 0.00 | 2.0 | 2.0 | <4.5 | 1.3 |
| 2 | 0.00 | 1.00 | 0.00 | 1.5 | >1.0 | <4.0 | 0.5 |

TABLE 7-continued

| | Fuel Additive Composition (lbs/1000 Barrels) | | | Storage Stability Data | | | |
|---|---|---|---|---|---|---|---|
| | | | | F-21-61 (149° C.) | | ASTM D-4625 (43° C.) | |
| Sample | DMCA[1] | MDA[2] | HHT[3] | Color | Deposits | Color | Deposits (mg/1000 mL) |
| 3 | 14.00 | 1.00 | 5.00 | 1.5 | 2.0 | <2.5 | 0.6 |
| 4 | 19.00 | 1.00 | 0.00 | 1.5 | 2.0 | <2.5 | 0.2 |
| 5 | 0.00 | 1.00 | 19.00 | <2.0 | 2.0 | <2.5 | 1.0 |

[1]DMCA = N,N-dimethylcyclohexylamine
[2]MDA = N,N-disalicylidene-1,2-propylenediamine
[3]HHT = 1,3-dicyclohexyl-5-(N,N-dimethyl-3'-aminopropyl)hexahydrotriazine

EXAMPLE 18

Fuel compositions of Table 8 utilize a base fuel which was obtained from Sweet Crude from Southwest and/or Central Louisiana. The stability of the base (unadditized) fuel is illustrated by Sample 1. Sample 3 of Table 8, illustrates the long and short term stability of a fuel composition containing HHT and MDA in combination with the fuel of Sample 1.

TABLE 8

| | Fuel Additive Composition (lbs/1000 Barrels) | | | Storage Stability Data | | | |
|---|---|---|---|---|---|---|---|
| | | | | F-21-61 (149° C.) | | ASTM D-4625 (43° C.) | |
| Sample | DMCA[1] | MDA[2] | HHT[3] | Color | Deposits | Color | Deposits (mg/1000 mL) |
| 1 | 0.00 | 0.75 | 0.00 | <2.5 | 3.0 | <5.5 | 6.5 |
| 2 | 14.25 | 0.75 | 0.00 | <3.0 | 5.0 | <6.0 | 6.0 |
| 3 | 0.00 | 0.75 | 14.25 | <3.0 | 4.0 | <4.5 | 3.8 |
| 4 | 10.50 | 0.75 | 3.75 | 2.5 | 3.0 | 5.0 | 5.0 |

[1]DMCA = N,N-dimethylcyclohexylamine
[2]MDA = N,N-disalicylidene-1,2-propylenediamine
[3]HHT = 1,3-dicyclohexyl-5-(N,N-dimethyl-3'-aminopropyl)hexahydrotriazine

EXAMPLE 19

Fuel compositions of Table 9 utilize a base fuel which was obtained from Nigerian Crude. The stability of the base (unadditized) fuel is illustrated by Sample 1.

TABLE 9

| | Fuel Additive Composition (lbs/1000 Barrels) | | | Storage Stability Data | | | |
|---|---|---|---|---|---|---|---|
| | | | | F-21-61 (149° C.) | | ASTM D-4625 (43° C.) | |
| Sample | DMCA[1] | MDA[2] | HHT[3] | Color | Deposits | Color | Deposits (mg/1000 mL) |
| 1 | 0.00 | 0.00 | 0.00 | <2.5 | 3.0 | 4.5 | 2.5 |
| 2 | 9.50 | 0.50 | 0.00 | 2.5 | 3.0 | 4.0 | 1.4 |
| 3 | 28.50 | 1.50 | 0.00 | 3.0 | 3.0 | <4.5 | 0.9 |
| 4 | 0.00 | 0.50 | 9.50 | 2.0 | 2.0 | <4.0 | 1.3 |
| 5 | 0.00 | 1.50 | 28.50 | 2.0 | 2.0 | <4.0 | 1.2 |

[1]DMCA = N,N-dimethylcyclohexylamine
[2]MDA = N,N-disalicylidene-1,2-propylenediamine
[3]HHT = 1,3-dicyclohexyl-5-(N,N-dimethyl-3'-aminopropyl)hexahydrotriazine

EXAMPLE 20

Fuel compositions of Table 10 utilize a base fuel which was obtained from Mid Continent Crude. The stability of the base (unadditized) fuel is illustrated by Sample 1. Samples 3 and 6 of Table 10, illustrate the long and short term stability of fuel compositions containing all three additive components (i.e. DMCA, MDA, HHT) in combination with the fuel of Sample 1.

TABLE 10

| | Fuel Additive Composition (lbs/1000 Barrels) | | | Storage Stability Data | | | |
|---|---|---|---|---|---|---|---|
| | | | | F-21-61 (149° C.) | | ASTM D-4625 (43° C.) | |
| Sample | DMCA[1] | MDA[2] | HHT[3] | Color | Deposits | Color | Deposits (mg/1000 mL) |
| 1 | 0.00 | 0.00 | 0.00 | 2.5 | 3.0 | <4.5 | 3.2 |
| 2 | 0.00 | 0.25 | 0.00 | <3.0 | 5.0 | <4.5 | 3.6 |
| 3 | 3.50 | 0.25 | 1.25 | <2.5 | 3.0 | <4.5 | 2.0 |
| 4 | 4.75 | 0.25 | 0.00 | 2.5 | 3.0 | <4.0 | 2.0 |
| 5 | 0.00 | 0.25 | 4.75 | <3.0 | 4.0 | 4.0 | 2.1 |
| 6 | 7.00 | 0.50 | 2.50 | 2.5 | 2.0 | <4.5 | 1.7 |
| 7 | 9.50 | 0.50 | 0.00 | 2.5 | 4.0 | <4.5 | 1.9 |

TABLE 10-continued

| | Fuel Additive Composition (lbs/1000 Barrels) | | | Storage Stability Data | | | |
|---|---|---|---|---|---|---|---|
| | | | | F-21-61 (149° C.) | | ASTM D-4625 (43° C.) | |
| Sample | DMCA[1] | MDA[2] | HHT[3] | Color | Deposits | Color | Deposits (mg/1000 mL) |
| 8 | 0.00 | 0.50 | 9.50 | 2.5 | 4.0 | <4.0 | 1.6 |

[1]DMCA = N,N-dimethylcyclohexylamine
[2]MDA = N,N-disalicylidene-1,2-propylenediamine
[3]HHT = 1,3-dicyclohexyl-5-(N,N-dimethyl-3'-aminopropyl)hexahydrotriazine

EXAMPLE 21

Fuel compositions of Table 11 utilize a base fuel which was obtained from Mid Continent Crude. The stability of the base (unadditized) fuel is illustrated by Sample 1. Samples 3 and 6 of Table 11, illustrate the long and short term stability of fuel compositions containing all three additive components (i.e. DMCA, MDA, HHT) in combination with the fuel of Sample 1.

TABLE 11

| | Fuel Additive Composition (lbs/1000 Barrels) | | | Storage Stability Data | | | |
|---|---|---|---|---|---|---|---|
| | | | | F-21-61 (149° C.) | | ASTM D-4625 (43° C.) | |
| Sample | DMCA[1] | MDA[2] | HHT[3] | Color | Deposits | Color | Deposits (mg/1000 mL) |
| 1 | 0.00 | 0.00 | 0.00 | <4.5 | 11.0 | <3.5 | 3.9 |
| 2 | 0.00 | 0.25 | 0.00 | <4.5 | 9.0 | 3.5 | 4.4 |
| 3 | 3.50 | 0.25 | 1.25 | 3.5 | 7.0 | <3.5 | 2.0 |
| 4 | 0.00 | 0.25 | 4.75 | 4.0 | 10.0 | <3.5 | 2.6 |
| 5 | 4.75 | 0.25 | 0.00 | <4.0 | 8.0 | <3.5 | 4.8 |
| 6 | 7.00 | 0.50 | 2.50 | <3.5 | 6.0 | 3.5 | 1.7 |
| 7 | 0.00 | 0.50 | 9.50 | <4.5 | 10.0 | <3.5 | 2.0 |
| 8 | 9.50 | 0.50 | 0.00 | 3.5 | 7.0 | 3.5 | 3.1 |

[1]DMCA = N,N-dimethylcyclohexylamine
[2]MDA = N,N-disalicylidene-1,2-propylenediamine
[3]HHT = 1,3-dicyclohexyl-5-(N,N-dimethyl-3'-aminopropyl)hexahydrotriazine

What is claimed is:

1. A liquid hydrocarbonaceous fluid comprising a minor stabilizing amount of one or a mixture of hexahydrotriazine compounds of the formula $$\begin{array}{c} R_1 \diagdown N \diagup \diagdown N \diagup R_2 \\ | \\ N \\ | \\ R_3 \\ | \\ R_4 \diagup N \diagdown R_5 \end{array}$$

wherein $R_1$ is a hydrocarbyl group; $R_2$ is either a hydrocarbyl group or a dihydrocarbyl aminoalkyl group; $R_3$ is an alkylene group having up to 12 carbon atoms, and $R_4$ and $R_5$ are hydrocarbyl groups.

2. The fluid of claim 1 wherein each of $R_1$ and $R_2$ is an alkyl group having from 2 to 24 carbon atoms; a cycloalkyl group having from 5 to 18 carbon atoms; or an aryl or substituted aryl group having 6 to 10 carbon atoms or a mixture thereof.

3. The fluid of claim 2 wherein $R_4$ and $R_5$ are the same or different alkyl groups having from 1 to 24 carbon atoms.

4. The fluid of claim 3 wherein $R_3$ is a propylene group.

5. The fluid of claim 1 wherein $R_4$ and $R_5$ are the same or different alkyl groups having from 1 to 24 carbon atoms.

6. The fluid of claim 1 wherein $R_1$ is a $C_4$ to $C_{18}$ alkyl or alkenyl group; a $C_6$ to $C_{10}$ cycloalkyl or cycloalkenyl group; or a $C_6$ to $C_{14}$ aryl group and $R_2$ is a di-($C_1$–$C_{20}$) alkyl aminopropylene group.

7. The fluid of claim 6 wherein $R_3$ is a trimethylene group and $R_4$ and $R_5$ are methyl groups.

8. The fluid of claim 1 wherein the hexahydrotriazine is a reaction product of cyclohexylamine, N,N-dimethyl-1,3-propane diamine, and formaldehyde.

9. A middle distillate fuel comprising a minor stabilizing amount of a hexahydrotriazine of the formula $$\begin{array}{c} R_1 \diagdown N \diagup \diagdown N \diagup R_2 \\ | \\ N \\ | \\ R_3 \\ | \\ R_4 \diagup N \diagdown R_5 \end{array}$$

wherein $R_1$ is a hydrocarbyl group; and $R_2$ is either a hydrocarbyl group or a dihydrocarbylaminoalkyl group; $R_3$ is an alkylene group having up to 12 carbon atoms; and $R_4$ and $R_5$ are hydrocarbyl groups.

10. A middle distillate fuel comprising a minor stabilizing amount of a hexahydrotriazine comprising the reaction product of cyclohexylamine, N,N-dimethyl-1,3-propane diamine, and formaldehyde.

11. The middle distillate fuel of claim 10 further comprising a metal deactivator.

12. The middle distillate fuel of claim 11 wherein the metal deactivator is N,N-disalicylidene-1,2-propylene diamine.

13. The middle distillate fuel of claim 12 further comprising N,N-dimethylcyclohexylamine.

14. A process for stabilizing a hydrocarbonaceous fuel comprising forming a mixture of said fuel and a stabilizing amount of a hexahydrotriazine of the formula

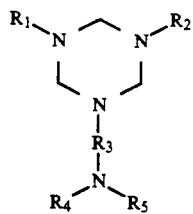

wherein $R_1$ is a hydrocarbyl group; $R_2$ is either a hydrocarbyl group or a dihydrocarbylaminoalkyl group; $R_3$ is an alkylene group having up to 12 carbon atoms; and $R_4$ and $R_5$ are hydrocarbyl groups.

15. The process of claim 14 wherein the hexahydrotriazine is the reaction product of cyclohexylamine, N,N-dimethyl-1,3-propane diamine, and formaldehyde.

16. The process of claim 15 wherein the mixture further comprises N,N-disalicylidene-1,2-propylene diamine.

17. The process of claim 16 further wherein the mixture further comprises N,N-dimethylcyclohexylamine.

* * * * *